(12) United States Patent
Lee et al.

(10) Patent No.: US 9,173,853 B2
(45) Date of Patent: Nov. 3, 2015

(54) COMPOSITION FOR GENE DELIVERY (71) Applicant: Chong Kun Dang Pharmaceutical Corp., Seoul (KR)

(72) Inventors: Young Nam Lee, Seoul (KR); Ho Young Hwang, Seoul (KR); Sang Myoung Noh, Seoul (KR); Hee-Jeong Cho, Seoul (KR); Ah-Reum Chae, Seoul (KR); Ji Hee Lee, Seoul (KR); Min Hyo Ki, Seoul (KR); Jong Lae Lim, Seoul (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 0 days.

(21) Appl. No.: 14/357,375

(22) PCT Filed: Nov. 9, 2012

(86) PCT No.: PCT/KR2012/009443
§ 371 (c)(1),
(2) Date: May 9, 2014

(87) PCT Pub. No.: WO2013/070010
PCT Pub. Date: May 16, 2013

(65) Prior Publication Data
US 2015/0110876 A1 Apr. 23, 2015

(30) Foreign Application Priority Data
Nov. 10, 2011 (KR) .................. 10-2011-0117082

(51) Int. Cl.
*A61K 9/51* (2006.01)
*A61K 48/00* (2006.01)
*C12N 15/113* (2010.01)
*A61K 47/36* (2006.01)
*A61K 9/00* (2006.01)
*A61K 47/18* (2006.01)
*A61K 9/127* (2006.01)
*A61K 9/19* (2006.01)
*C12N 15/88* (2006.01)
*C12N 15/11* (2006.01)

(52) U.S. Cl.
CPC ............. *A61K 9/5161* (2013.01); *A61K 9/0019* (2013.01); *A61K 9/127* (2013.01); *A61K 9/19* (2013.01); *A61K 9/51* (2013.01); *A61K 9/5123* (2013.01); *A61K 9/5169* (2013.01); *A61K 47/183* (2013.01); *A61K 47/36* (2013.01); *A61K 48/0041* (2013.01); *C12N 15/111* (2013.01); *C12N 15/113* (2013.01); *C12N 15/1135* (2013.01); *C12N 15/1136* (2013.01); *C12N 15/88* (2013.01); *C12N 2310/11* (2013.01); *C12N 2310/12* (2013.01); *C12N 2310/14* (2013.01); *C12N 2310/351* (2013.01); *C12N 2320/32* (2013.01)

(58) Field of Classification Search
None
See application file for complete search history.

(56) References Cited

U.S. PATENT DOCUMENTS

| 7,361,640 B2 | 4/2008 | Huang et al. |
| 2003/0068277 A1 | 4/2003 | Vanbever et al. |
| 2003/0212031 A1 | 11/2003 | Huang et al. |
| 2010/0040694 A1 | 2/2010 | Nah et al. ............... 424/489 |
| 2010/0113559 A1 | 5/2010 | Park et al. ............... 514/44 A |
| 2011/0038941 A1 | 2/2011 | Lee et al. |
| 2014/0206616 A1 | 7/2014 | Ko et al. |

FOREIGN PATENT DOCUMENTS

| JP | A 2010-515678 | 5/2010 |
| WO | WO 99/36089 | 7/1999 |
| WO | WO 03/030941 | 4/2003 |
| WO | WO 03030941 A1 * | 4/2003 |
| WO | WO 2004/074314 | 9/2004 |

OTHER PUBLICATIONS

Rojanarata ("Chitosan-Thiamine Pyrophosphate as a Novel Carrie for siRNA Delivery," Pharmaceutical Research, 2008, 25(12):2807-2814.*
Wang, J. et al., "Delivery of siRNA Therapeutics: Barriers and Carriers," The AAPS Journal, 2010, 12(4):492-503.
Lappalainen, K. et al., "Comparison of Cell Proliferation and Toxicity Assays Using Two Cationic Liposomes," Pharmaceutical Research, 1994, 11(8):1127-1131.
Prashanth, K.V. et al., "Chitin/chitosan: modifications and their unlimited application potential—an overview," Trends in Food Science & Technology, 2007, 18:117-131.
Rojanarata, T. et al., "Chitosan-Thiamine Pyrophosphate as a Novel Carrier for siRNA Delivery," Pharmaceutical Research, 2008, 25(12):2807-2814.
Karmali, P. et al., "Interactions of nanoparticles with plasma proteins: implication on clearance and toxicity of drug delivery systems," Expert Opinion DD, 2011, 8(3):343-357.
U.S. Appl. No. 14/440,058, filed Dec. 27, 2013.
U.S. Appl. No. 14/440,059, filed Dec. 27, 2013.
U.S. Appl. No. 14/440,060, filed Dec. 27, 2013.

(Continued)

*Primary Examiner* — H. Sarah Park
(74) *Attorney, Agent, or Firm* — Dentons US LLP; Stephanie Seidman; Frank J. Miskiel (57) ABSTRACT

Disclosed is a pharmaceutical composition for gene delivery, comprising: (i) a gene; (ii) a water-soluble chitosan; (iii) a thiamine pyrophosphate or a pharmaceutically acceptable salt thereof; (iv) a protamine or a pharmaceutically acceptable salt thereof; and (v) a neutral or anionic phospholipid. The composition can introduce a gene into cells safely and effectively. Composed of non-toxic and injectable components, the composition is safe for the body and can be advantageously commercialized. Notably, it can deliver a gene at high efficiency in vivo as well as in vitro, and is stable in the blood.

8 Claims, 3 Drawing Sheets

(56) References Cited

OTHER PUBLICATIONS

Letter/Written Disclosure of the Supplemental Information Disclosure Statement for the above-referenced applicaiton, mailed May 29, 2015, 2 pages.

Kumar et al., "Chitosan IFN-γ-pDNA Nanoparticle (CIN) Therapy for allergic asthma," Genetic Vaccines and Therapy 1(3):1-10 (2003).

International Search Report and Written Opinion, issued Mar. 26, 2013, in connection with International Patent Application No. PCT/KR2012/009443, 6 pages.

International Preliminary Report on Patenability, issued May 13, 2014, in connection with International Patent Application No. PCT/KR2012/009443, 4 pages.

Letter/Written Disclosure of the Supplemental Information Disclosure Statement for the above-referenced application, submitted Jul. 20, 2015, 3 pages.

"Molecular Action of Protamine on Gene Introduction by Using Positively Charged Liposome" The Journal of Japanese Biochemical Society 1P-689, 73(8):795 (2001) [in Japanese language with English translation].

Chono et al. "An efficient and low immunostimulatory nanoparticle formulation for systemic siRNA delivery to the tumor." Journal of Controlled Release 131:64-69 (2008).

Mao et al. "Chitosan-based formulations for delivery of DNA and siRNA." Advanced Drug Delivery Reviews 62:12-27 (2010).

Tanaka et al. "The Freeze-Drying of Liposome with Saccharides and their Protection Mechanism." Membrane 18(3):156-163 (1993) [in Japanese language with English language abstract].

Welz et al. "Nuclear transport of oligonucleotides in HepG2-cells mediated by protamine sulfate and negatively charged liposomes." Pharm Res. 17(10):1206-1211 (2000).

Office Action, mailed May 12, 2015, in connection with Japanese Patent Application No. 2014-540950 [English translation with original document in Japanese], 6 pages.

Extended European Search Report, issued Jun. 15, 2015, in connection with European Patent Application No. 12847217.2, 5 pages.

\* cited by examiner

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Survivin siRNA sense sequence
<220> FEATURE:
<221> NAME/KEY: modified_base
<222> LOCATION: (20)
<223> OTHER INFORMATION: t is deoxy t (dT)
<220> FEATURE:
<221> NAME/KEY: modified_base
<222> LOCATION: (21)
<223> OTHER INFORMATION: t is deoxy t (dT)

<400> SEQUENCE: 1
aaggagauca acauuuucat t                                                 21

<210> SEQ ID NO 2
<211> LENGTH: 21
<212> TYPE: DNA
<213> ORGANISM: Artificial Sequence
<220> FEATURE:
<223> OTHER INFORMATION: Survivin siRNA antisense sequence
<220> FEATURE:
<221> NAME/KEY: modified_base
<222> LOCATION: (20)
<223> OTHER INFORMATION: t is deoxy t (dT)
<220> FEATURE:
<221> NAME/KEY: modified_base
<222> LOCATION: (21)
<223> OTHER INFORMATION: t is deoxy t (dT)

<400> SEQUENCE: 2
ugaaaauguu gaucuccuut t                                                 21

<210> SEQ ID NO 3
<211> LENGTH: 21
<212> TYPE: DNA
<213> ORGANISM: Artificial Sequence
<220> FEATURE:
<223> OTHER INFORMATION: VEGF siRNA sequence
<220> FEATURE:
<221> NAME/KEY: modified_base
<222> LOCATION: (20)
<223> OTHER INFORMATION: t is deoxy t (dT)
<220> FEATURE:
<221> NAME/KEY: modified_base
<222> LOCATION: (21)
<223> OTHER INFORMATION: t is deoxy t (dT)

<400> SEQUENCE: 3
ggaguacccu gaugagauct t                                                 21
```

```
<210> SEQ ID NO 4
<211> LENGTH: 18
<212> TYPE: DNA
<213> ORGANISM: Artificial Sequence
<220> FEATURE:
<223> OTHER INFORMATION: Gataparsen sequence
<220> FEATURE:
<221> NAME/KEY: modified_base
<222> LOCATION: (1)
<223> OTHER INFORMATION: u is
      deoxy(phosphorothioate)[2'-O-(2-methoxyethyl)]5-methyl-ribonucleo-
      uridine (= d(P-thio)[2'-O-(2-methoxyethyl)]m5rU)
<220> FEATURE:
<221> NAME/KEY: modified_base
<222> LOCATION: (2)
<223> OTHER INFORMATION: G is [2'-O-(2-methoxyethyl)]ribonuleo-guanine
      (= [2'-O-(2-methoxyethyl)]rG)
<220> FEATURE:
<221> NAME/KEY: modified_base
<222> LOCATION: (3)
<223> OTHER INFORMATION: U is [2'-O-(2-methoxyethyl)]5-methyl-
      ribonucleo-uridine (= [2'-O-(2-methoxyethyl)]m5rU)
<220> FEATURE:
<221> NAME/KEY: modified_base
<222> LOCATION: (4)
<223> OTHER INFORMATION: G is [2'-O-(2-methoxyethyl)]ribonucleo-guanine
      (= [2'-O-(2-methoxyethyl)]rG)
<220> FEATURE:
<221> NAME/KEY: modified_base
<222> LOCATION: (5)
<223> OTHER INFORMATION: C is 5-methylcytidine (= m5C)
<220> FEATURE:
<221> NAME/KEY: modified_base
<222> LOCATION: (10)
<223> OTHER INFORMATION: C is 5-methylcytidine (= m5C)
<220> FEATURE:
<221> NAME/KEY: modified_base
<222> LOCATION: (15)
<223> OTHER INFORMATION: A is [2'-O-(2-methoxyethyl)]ribonucleo-adenine
      (= [2'-O-(2-methoxyethyl)]rA)
<220> FEATURE:
<221> NAME/KEY: modified_base
<222> LOCATION: (16)
<223> OTHER INFORMATION: A is [2'-O-(2-methoxyethyl)]ribonucleo-adenine
      (= [2'-O-(2-methoxyethyl)]rA)
<220> FEATURE:
<221> NAME/KEY: modified_base
<222> LOCATION: (17)
<223> OTHER INFORMATION: U is [2'-O-(2-methoxyethyl)]5-methyl-
      ribonucleo-uridine (= [2'-O-(2-methoxyethyl)]m5rU)
<220> FEATURE:
<221> NAME/KEY: modified_base
<222> LOCATION: (18)
<223> OTHER INFORMATION: U is [2'-O-(2-methoxyethyl)]5-methyl-
      ribonucleo-uridine (= [2'-O-(2-methoxyethyl)]m5rU)

<400> SEQUENCE: 4
ugugctattc tgtgaauu                                                   18

<210> SEQ ID NO 5
<211> LENGTH: 21
<212> TYPE: DNA
<213> ORGANISM: Artificial Sequence
<220> FEATURE:
<223> OTHER INFORMATION: Fluorescein-labeled ds RNA sequence
<220> FEATURE:
<221> NAME/KEY: modified_base
<222> LOCATION: (20)
<223> OTHER INFORMATION: t is deoxy t (dT)
<220> FEATURE:
<221> NAME/KEY: modified_base
<222> LOCATION: (21)
<223> OTHER INFORMATION: t is deoxy t (dT)
```

```
<400> SEQUENCE: 5
uuguuuugga gcacggaaat t                                      21
```

COMPOSITION FOR GENE DELIVERY

CROSS-REFERENCE TO RELATED APPLICATIONS

This application is a national stage application of PCT/KR2012/009443, filed Nov. 9, 2012 and published as WO 2013/070010 on May 16, 2013, which claims the benefit of Korean application no. 10-2011-0117082, filed Nov. 10, 2011, the entirety of each of which is incorporated herein by reference.

TECHNICAL FIELD

The present invention relates to a nanoparticle composition for gene delivery using the chitosan as a cationic polymer.

BACKGROUND ART

Up To date, research for intracellular gene delivery has been conducted. Also, attempts to apply the research results to the development of practically available therapeutic agents have been conducted. Genes are genetic materials that contain nucleotides and polynucleotides, that is, nucleic acids. Genes has a strong negative charge because of the nucleotide unit. Genes are readily degraded by various enzymes that exist in vivo and in vitro, and have a short half life within cells or in vivo. Accordingly, all gene therapeutic agents based nucleic acid must be accompanied with development of therapeutic agents and delivery technology thereof.

Transfection is the process of introducing genetic agent into eukaryotic cells. It is the technology required in the research of basic sciences, including cytology, molecular biology, study of genetic functions and drug targets, etc. Also, it plays a core role for developing practical medicine in research of applied sciences including pharmacology, pharmaceutics, etc. Techniques for the delivery of genes into cells generally have been studied about the using of viral and non-viral carriers.

Currently, virus vector are used generally. The virus-mediated gene transfer has very high efficiency of gene transfer, but virus-mediated gene transfer may cause an immune response and thus is difficult to apply over a long period of time. In addition, it cannot completely exclude the possibility of pathogenic virus replication. In contrast, non-viral carriers have the advantage of delivering genetic materials without the risk of viral carriers (The AAPS Journal, 2010; 12: 492-503). In order to overcoming the risk of viral carriers, cationic lipids or polymers which are associable with anionic genes are used for non-viral delivery method.

U.S. Pat. No. 7,361,640 discloses claimed a non-covalent complex of gene/lipid/polycation, which is formed by adding a gene to a solution consisting of at least one the cationic lipid and the polycation. However, the cationic lipid species used in the complex exhibits cytotoxicity (Pharmaceutical Research 1994; 11: 1127-1131).

In addition, cationic lipids are not suitable for mass production because material need synthesis and a high degree of purification and is difficult to control their quality. In addition, it is difficult to commercialization because it is unstable during storage and distribution.

U.S. Patent Publication No. 2011/0038941 discloses the method for the preparing of oligonucleotide-lipid nanoparticle consisting of an oligonucleotide, a lipid and a complex agent, (1) mixing a lipid, a complexing agent and a cationic polymer in a water miscible organic solvent, (2) dissolving an oligonucleotide in an aqueous buffer, (3) injecting the mixture of step (1) into the mixture of step (2), or mixing the mixture of step (1) and the mixture of step (2) under pressure, to form a final mixture; and (4) removing the organic solvent from the final mixture to form the oligonucleotide-lipid nanoparticle. This preparing method is difficult to apply to industrial practice because it does not ensure the quality, it requires special instruments and mass production is difficult.

U.S. Patent Publication No. 2003/0068277 discloses the method for the preparing of complex composition of a polycationic complexing agent comprising protamine, spermine, spermidine, or chitosan and a phospholipid, but complex is designed for delivery of proteins to the pulmonary system by inhalation.

In preparing of gene delivery complex, chitosan is a cationic material which can be produced on a mass scale, abundantly found in nature, and is of high biocompatibility. Chitosan has attracted considerable interest as a non-viral carrier candidate for use in gene delivery. Notably, when administered to the body, chitosan is broken down by a lysozyme to amine sugar. It is a natural polymer which is as highly safe to the body as an LD50 of 16 g/kg in rats (Trends in Food Science & Technology, 2007; 18: 117-131).

Although it is considered as a potent candidate for a non-viral carrier which can form a complex with a gene through ionic bonds and transfer the gene into cells, chitosan is problematic in that its positive charge density is lowered at the physiological pH (pH 7~7.4), which leads to poor binding affinity with genes. After all, chitosan does not maintain a complex form with genes in the physiological pH condition so that the genes dissociate from chitosan, with significantly poor delivery to cells.

Theerasak Rojanarata et al. prepared chitosan-thiamine pyrophosphate by using excess thiamine pyrophosphate as acid agent for dissolving chitosan, which is insoluble at the physiological pH and suggested the chitosan-thiamine pyrophosphate as a gene carrier (Pharmaceutical Research 2008; 25: 2807-2814).

The nanocomplex of chitosan and thiamine pyrophosphate, disclosed by Theerasak Rojanarata et al., was evaluated to deliver genes at high rates in vitro, but not in vivo. As opposed to in vitro, various serum proteins and cellular exudates exist in vivo. Therefore, when administered to the body, chitosan nanoparticles aggregate with serum proteins and cellular exudates in vivo and finally precipitate with the concomitant loss of gene delivery performance. For this reason, conventional chitosan complexes are reportedly known to exhibit poor gene delivery performance in vivo and to fail in commercialization as gene carriers (Expert Opinion on Drug Delivery, 2011; 8: 343-357).

REFERENCE

Patent Document

U.S. Patent Publication No. 2003/0212031 (Nov. 13, 2003)
Korean Patent Laid-Open Publication No. 10-2004-0058199 (Jul. 3, 2004)

DISCLOSURE OF INVENTION

Technical Problem

The present invention aims to provide a composition for gene delivery, which is highly biostable in vivo and exhibits outstanding gene delivery efficiency, and a method for preparing the same.

Solution to Problem

The inventors of the present invention intensively have been studied to overcome problems encountered biostability in vivo as well as in vitro, excellent gene delivery, non-toxicity to the body and the composition which can be commercialized into drug products. As a result, surprisingly, a composition comprising nanoparticle composed of a gene, a water-soluble chitosan, a thiamine pyrophosphate, a protamine, and a neutral or anionic phospholipid exhibit biostable nanoparticle in vivo as well as in vitro, and thus can perform excellent gene delivery.

SUMMARY OF THE INVENTION

The present invention provides a pharmaceutical composition for gene delivery, comprising (i) a gene, (ii) a water-soluble chitosan, (iii) a thiamine pyrophosphate, (iv) a protamine, and (v) a neutral or anionic phospholipid, and a method for preparing the same.

In order to be developed into a commercial product for gene delivery, as mentioned previously, chitosan nanoparticles should simultaneously retain high biostability in the blood as well as binding affinity with genes. If either of these is of poverty, the administrating to the body is impossible. The nanoparticles of the present invention lack the problems with conventional chitosan nanoparticles, that is, they do not decrease in the strength of the ionic bond with genes in the physiological pH condition and are prevented from aggregating with serum proteins and cellular exudates in vivo. Accordingly, the nanoparticles of the present invention exhibit high stability in the blood. Nowhere are these surprising effects of the nanoparticles of the present invention mentioned in previous studies on gene delivery with chitosan.

Here, the present invention overcomes problems which chitosan has not yet been commercialized as a gene carrier in spite of being a natural material, provides a novel composition for gene delivery which is superior in terms of biostability and gene delivery performance.

Constitution

The present invention provides a pharmaceutical composition for gene delivery, comprising (i) a gene, (ii) a water-soluble chitosan, (iii) a thiamine pyrophosphate, (iv) a protamine, and (v) a neutral or anionic phospholipid. Also, the present invention provides a method for preparing the same.

As used herein, the term "gene" is genetic materials that contain nucleotides and polynucleotides, that is, nucleic acids. It is intended to encompass any genetic material including a stretch of a polynucleotide that codes for a polypeptide having a function or effect of interest in the organism when it is introduced into cells. The genes may be at least one selected from the group consisting of a single- or double-stranded DNA (deoxyribonucleic acid), a single- or double-stranded RNA, a plasmid DNA, a single- or double-stranded siRNA (small interfering RNA), an antisense oligonucleotide, a ribozyme, an enzymatic RNA, and a nucleotide. Preferably, the gene is at least one selected from among a plasmid DNA, a single- or double-stranded siRNA, and an antisense oligonucleotide. The gene may be a gene therapy drug. Herein, the term "gene therapy drug" is meant a gene that is useful for the therapy or prevention of one or more diseases.

Used in the present invention, chitosan is a natural cationic polysaccharide having (1→4) 2-amine-2-deoxy-β-D-glucan as a structural unit and is very safe to the body. Chitosan is produced as a polymer with free amine groups by deacetylation of chitin, which is the structural element in the exoskeleton of crustaceans. Herein, chitosan ranges in molecular weight from 1 to 500 kDa with a content of free amine groups of 50% or higher, and preferably in molecular weight from 150 to 400 kDa with a content of free amine groups of 80% or higher, but do not limit the present invention.

With regard to the solubilization of chitosan, water-soluble chitosan, insoluble chitosan, and chitosan derivatives fall within the scope of the present invention, with preference for water-soluble chitosan. The water-soluble chitosan useful in the present invention may be at least one selected from the group consisting of chitosan HCl, chitosan acetate, chitosan glutamate and chitosan lactate. The water-soluble chitosan can be soluble in water when its intramolecular amine group form salts with equivalents of acids such as HCl, acetic acid, glutamic acid, lactic acid, etc. For use in injections, water-soluble chitosan can be purified by removing bacteria or impurities therefrom, whereas when water-insoluble chitosan is insoluble in both water and organic solvents, the removal of bacteria or impurities therefrom is difficult. Thus, insoluble chitosan may be used for study, but is difficult to apply to medicines for injection.

Used in the present invention, when vitamin B1 is administrated to the body, thiamine pyrophosphate is formed. Thiamine pyrophosphate is an active form of vitamin B1 which is produced in vivo and stable material. Thiamine pyrophosphate functions to supplement the weak bond between chitosan and the gene because it has both negative and positive charges. Thiamine pyrophosphate in the present invention includes pharmaceutically acceptable salts of thiamine phosphate and thiamine phosphate itself.

Used in the present invention, protamines are natural cationic proteins rich in arginine and are abundantly found in animal sperms, notably sperm nuclei of fishes including salmon. Protamines function like histones by association with and dissociation from genes. Typically, the protamines extracted from sperm nuclei of fishes have a molecular weight of about 4,000 to 10,000 kDa with arginine accounting for about 70% of the constituent amino acids thereof, but do not limit the present invention. Protamines in the present invention include protamines themselves and their pharmaceutically acceptable salts. In detail, the pharmaceutically acceptable salts of protamines include acid addition salts such as hydrochloride and sulfate.

Because protamines themselves as well as their salts are soluble in water, any form of protamines may be used in the composition for gene delivery according to the present invention.

Used in the present invention, phospholipids contain structurally alkyl esters for non-polar tails and a phosphoric acid for a polar head. Neutral and anionic phospholipids are electrically neutral and negative on the head moiety, respectively. Cationic phospholipids, although able to perform gene delivery, are toxic and thus difficult to use as a medicinal excipient. In the neutral or anionic phospholipids useful in the present invention, the non-polar tail moiety may be a saturated or unsaturated alkyl ester of 4 to 30 carbon atoms while the polar head moiety is a phosphoric acid selected from phosphatidylcholine, phosphatidylethanolamine, phosphatidylserine, phosphatidylglycerine, phosphatidylinositol, phosphatidic acid, sphingomyelin, phosphatidylcholine-N-methoxy polyethylene glycol, phosphatidylethanolamineN-methoxy polyethylene glycol, phosphatidylserine-N-methoxy polyethylene glycol, phosphatidic acid methoxy polyethylene glycol, and a mixture thereof. Also, the neutral or anionic phospholipids may be derived from plants such as beans or animals such as from eggs. The alkyl esters which account for the tails of neutral or anionic phospholipids may be saturated fatty acid esters such as mono- and di-palmitoyl, mono- and dimyristoyl, mono- and di-lauryl, and mono- and di-stearyl, unsaturated fatty acid esters such as mono- and di-linoleyl, mono- and di-oleyl, mono- and di-palmitoyl, and mono- and di-myristoleyl, or a combination of saturated and unsaturated fatty acid esters.

The composition for gene delivery of comprising above elements may be prepared illustrative method, but do not limit the present invention. As an example, the composition of the present invention may be prepared following method; (1) mixing a gene and a protamine in a suitable solvent, preferably sterile distilled water or saline, to form a pre-complex, and (2) adding chitosan, thiamine pyrophosphate, and a neutral or anionic phospholipid to the pre-complex to form a final nanoparticle. As another example, the composition of the present invention may be prepared following method; (1) mixing a gene, chitosan, and thiamine pyrophosphate in water to form a pre-complex, and (2) adding a protamine and a neutral or anionic phospholipid to the pre-complex to form a final nanoparticle. Herein, the solvent may be used in an amount of about 1 mL or less per mg of the gene. The nanoparticle may be 10~500 nm in diameter, and preferably 10~300 nm in diameter, in order to meet the drop size that is required for the introduction of intracellular.

In order to form nanoparticles, the composition of the present invention may contain chitosan in an amount of from 10 to 3,000 weight parts, thiamine pyrophosphate in an amount of from 1 to 1,000 weight parts, a protamine in an amount of from 10 to 1,000 weight parts and a neutral or anionic phospholipid in an amount of from 100 to 5,000 weight parts based on 100 weight parts of a gene. Preferably, chitosan is used in an amount of from 40 to 2,000 weight parts, thiamine pyrophosphate in an amount of from 20 to 500 weight parts, a protamine in an amount of from 10 to 700 weight parts, and a neutral or anionic phospholipid in an amount of from 500 to 5,000 weight parts, per 100 weight parts of a gene.

The composition for gene delivery in the form of nanoparticles in accordance with the present invention may be utilized as it is or may be formulated along with a pharmaceutically acceptable vehicle. To quote an example, the composition for gene delivery of the present invention may be formulated into various forms such as injections, drips, inhalants, etc. The pharmaceutically acceptable vehicles and the formulations are understood to persons having ordinary skill in the art.

In addition, the composition for gene delivery of the present invention may further comprise a sugar so as to prevent the nanoparticles from being degraded or deformed during storage or distribution. Example of the sugar is at least one selected from mannose, glucose, fructose, arabinose, mannitol, sorbitol, sucrose, trehalose, maltose, lactose, cellobiose, isomaltose, dextran, dextrin, α-cyclodextrin, β-cyclodextrin, γ-cyclodextrin, hydroxypropyl-β-cyclodextrin, hydroxyethyl-β-cyclodextrin, dimethyl-β-cyclodextrin, trimethyl-β-cyclodextrin and sulfobutylether β-cyclodextrin.

Also, the composition for gene delivery of the present invention may further comprise a pharmaceutically acceptable additive such as a stabilizer or buffer, a preservative, an analgesic, and an isotonic additive. Herein, the stabilizer includes an antioxidant, a reductant, and a chelating agent. The buffer aims to adjust pH and contain organic or inorganic salts. Examples of the preservative include paraoxybenzoic acid methyl, paraoxybenzoic acid ethyl, paraoxybenzoic acid propyl, paraoxybenzoic acid butyl, chlorobutanol, benzalkonium chloride, benzethonium chloride, phenol, cresol, chlorocresol, and benzyl alcohol. The analgesic may be a local anesthesia such as benzyl alcohol and chlorobutanol. The isotonic additive is used to adjust osmosis and may contain sugars and inorganic salts.

The composition for gene delivery of the present invention may be in a lyophilized form under the protection of the sugar. Given a lyophilized form, the composition may be rehydrated in a suitable buffer, for example, sterile saline, before use. A carrier suitable for use in reconstitution into a dosage form for intravenous injection may include physiological saline or phosphate buffered saline (PBS), a thickener, and a solubilizer, e.g., glucose, polyethylene glycol, polypropylene glycol and mixture thereof.

The composition for gene delivery of the present invention may be administered to mammals including humans via a suitable route, for example, by injection, intrapulmonarily, intranasaly, orally, or rectally. Preferably, it may be injected intravenously, intramuscularly, subcutaneously, intrauterinely, or intracranially. If necessary, the composition may be directly injected into tissues, organs, and tumors of interest.

The effective dosage of the composition in accordance with the present invention may vary depending on various factors, including dosage form, route of administration, purpose of administration, the patient's age and weight, severity of disease, etc. Generally, the composition for gene delivery according to the present invention may be administered at a daily dose of the active ingredient ranging from 1 µg to 200 mg/kg. The dose may vary with various factors.

Because all of its components are free of cytotoxicity and are injectable, the composition is safe for the body and is advantageous in commercialization into medicinal products.

Advantageous Effects of Invention

The composition for gene delivery of the present invention can introduce a gene into cells safely and effectively. Composed of non-toxic and injectable components, the composition is safe for the body and can be advantageously commercialized. Notably, the composition for gene delivery of the present invention can deliver a gene with high efficiency in vivo as well as in vitro, and is stable in the blood.

MODE FOR THE INVENTION

A better understanding of the present invention may be obtained through the following examples which are set forth to illustrate, but are not to be construed as limiting, the present invention.

EXAMPLES

Examples 1 to 4

Preparation of Composition for Survivin siRNA Delivery

Four milligrams of 150~400 kDa chitosan HCl (FMC CL214, FMC), 2 mg of thiamine pyrophosphate (Sigma Aldrich), and 0.5 mg of protamine sulfate (Alps Pharmaceutical) were independently dissolved in 1 mL of sterile distilled water. Each solution was filtered through a 0.22 μm filter. Survivin siRNA (Bioneer) was dissolved to a final concentration of 1 mg/mL in sterile distilled water. Lipoid S-100 (Lipoid) as phospholipid and distearoyl-glycero-phosphoethanolamine-methyl polyethylene glycol-2000 (DSPE-mPEG2000) (Lipoid PE 18:0/18:0-PEG 2000, Lipoid) were dissolved at the ratios given in Table 1 in 1 mL of ethanol with the total phospholipid weight amounting to 30 mg, followed by filtration through a 0.22 μm filter. The survivin siRNA solution was mixed at the ratios given in Table 1 with the protamine solution to form pre-complexes and then mixed with the water-soluble chitosan solution, the thiamine pyrophosphate solution, and the phospholipid solution to prepare compositions containing nanoparticles. Herein, the sequence of survivin siRNA composed of sense: 5'-AAG GAG AUC AAC AUU UUC A(dTdT)-3', and antisense: 5'-UGA AAA UGU UGA UCU CCU U(dTdT)-3' were used.

In Table 1, the unit is weight (μg).

TABLE 1

|  | Ex. 1 | Ex. 2 | Ex. 3 | Ex. 4 |
| --- | --- | --- | --- | --- |
| Survivin siRNA | 1 | 1 | 1 | 1 |
| Chitosan HCl | 17.1 | 17.1 | 8.6 | 8.6 |
| Thiamine Pyrophosphate | 2.9 | 2.9 | 2.9 | 2.9 |
| Protamine | 0.6 | 0.6 | 5 | 5 |
| Lipoid S-100[1] | 32 | 30.4 | 32 | 30.4 |
| DSPE-mPEG2000 | 0 | 1.6 | 0 | 1.6 |

[1] Lipoid S-100 is composed of phosphatidylcholine, phosphatidylethanolamine, phosphatidylinositol, and phosphatidylcholine, with the content of phosphatidylcholine amounting more than 94%.

Examples 5 to 8

Preparation of Composition for VEGF siRNA Delivery

Four milligrams of 150~400 kDa chitosan HCl, 2 mg of thiamine pyrophosphate, and 0.5 mg of protamine sulfate (Alps Pharmaceutical) were independently dissolved in 1 mL of sterile distilled water. Each solution was filtered through a 0.22 μm filter. Vascular endothelial growth factor (VEGF) siRNA (Bioneer) was dissolved to a final concentration of 1 mg/mL in sterile distilled water. Lipoid S-100 as phospholipid and DSPE-mPEG2000 were dissolved at the ratios given in Table 2 in 1 mL of ethanol with the total phospholipid weight amounting to 30 mg, followed by filtration through a 0.22 μm filter. The VEGF siRNA solution was mixed at the ratios given in Table 2 with the water-soluble chitosan solution and the thiamine pyrophosphate solution to form pre-complexes, and then mixed with the protamine solution and the phospholipid solution to prepare compositions containing nanoparticles. Herein, the sequence of the VEGF siRNA was 5'-GGA GUA CCC UGA UGA GAU C(dTdT)-3'.

In Table 2, the unit is weight (μg).

TABLE 2

|  | Ex. 5 | Ex. 6 | Ex. 7 | Ex. 8 |
| --- | --- | --- | --- | --- |
| VEGF siRNA | 1 | 1 | 1 | 1 |
| Chitosan HCl | 17.1 | 17.1 | 8.6 | 8.6 |
| Thiamine Pyrophosphate | 2.9 | 2.9 | 2.9 | 2.9 |
| Protamine | 0.6 | 0.6 | 5 | 5 |
| Lipoid S-100 | 32 | 30.4 | 32 | 30.4 |
| DSPE-mPEG2000 | 0 | 1.6 | 0 | 1.6 |

Examples 9 to 14

Preparation of Composition for Gataparsen Delivery

Four milligrams of 150~400 kDa chitosan HCl, 2 mg of thiamine pyrophosphate, and 0.5 mg of protamine sulfate (Alps Pharmaceutical) were independently dissolved in 1 mL of sterile distilled water. Each solution was filtered through a 0.22 μm filter. A gataparsen (survivin antisense, Bioneer) was dissolved to a final concentration of 1 mg/mL in sterile distilled water. Lipoid S-100 and DSPE-mPEG2000 were dissolved at the ratios given in Table 3 in 1 mL of ethanol with the total phospholipid weight amounting to 30 mg, followed by filtration through a 0.22 μm filter. The gataparsen (survivin antisense) solution was mixed at the ratios given in Table 1 with the protamine solution to form pre-complexes and then mixed with the water-soluble chitosan solution, the thiamine pyrophosphate solution, and the phospholipid solution to prepare composition containing nanoparticles. Herein, gataparsen has the sequence of 3'-d(P-thio)([2'-O-(2-methoxyethyl)]m5rU-[2'-O-
(2-methoxyethyl)]rG-[2'-O-(2-methoxyethyl)]m5rU-
[2'-O-(2-methoxyethyl)]rG-m5C-T-A-T-T-m5C-T-G-T-
G-[2'O-(2-methoxyethyl)]rA-[2'-O-(2-
methoxyethyl)]rA-[2'-O-(2-methoxyethyl)]m5rU-
[2'-O-(2-methoxyethyl)]m5rU)-5'.

In Table 3, the unit is weight (μg).

TABLE 3

|  | Ex. 9 | Ex. 10 | Ex. 11 | Ex. 12 | Ex. 13 | Ex. 14 |
| --- | --- | --- | --- | --- | --- | --- |
| Gataparsen | 1 | 1 | 1 | 1 | 1 | 1 |
| Chitosan HCl | 17.1 | 17.1 | 1.7 | 1.7 | 0.43 | 0.43 |
| Thiamine Pyrophosphate | 2.9 | 2.9 | 0.3 | 0.3 | 0.07 | 0.07 |
| Protamine | 0.6 | 0.6 | 0.2 | 0.2 | 0.2 | 0.2 |
| Lipoid S-100 | 32 | 30.4 | 12 | 11.4 | 6 | 5.7 |
| DSPE-mPEG2000 | 0 | 1.6 | 0 | 0.6 | 0 | 0.3 |

Examples 15 to 17

Preparation of Lyophilized Composition for Survivin siRNA Delivery

Four milligrams of 150~400 kDa chitosan HCl, 2 mg of thiamine pyrophosphate, and 0.5 mg of protamine sulfate (Alps Pharmaceutical) were independently dissolved in 1 mL of sterile distilled water. Each solution was filtered through a 0.22 μm filter. A survivin siRNA was dissolved to a final concentration of 1 mg/mL in sterile distilled water. Lipoid S-100 30 mg was dissolved in 1 mL of ethanol, followed by filtration through a 0.22 μm filter. The survivin si RNA solution was mixed at the ratios given in Table 4 with the protamine solution to form pre-complexes and then mixed with the water-soluble chitosan solution, the thiamine pyrophosphate solution, and the phospholipid solution to prepare compositions containing nanoparticles. Herein, the survivin siRNA had the same sequence as in Examples 1 to 4. To the compositions was added a 30% solution of a sugar excipient (trehalose (Trehalose SG, Hayashibara), glucose) in sterile distilled water at ratios given in Table 4. The solutions were lyophilized at −70° C. to form solid phases.

In Table 4, the unit is weight (μg).

TABLE 4

|  | Ex. 15 | Ex. 16 | Ex. 17 |
|---|---|---|---|
| Survivin siRNA | 1 | 1 | 1 |
| Chitosan HCl | 17.1 | 17.1 | 17.1 |
| Thiamine Pyrophosphate | 2.9 | 2.9 | 2.9 |
| Protamine | 0.6 | 0.6 | 0.6 |
| Lipoid S-100 | 32 | 32 | 32 |
| Trehalose | 600 | 300 | 300 |
| Glucose | 0 | 150 | 300 |

COMPARATIVE EXAMPLES

Comparative Example 1

Preparation of Composition Consisting of Gene, Protamine, Thiamine Pyrophosphate, and Phospholipid A composition containing nanoparticles was prepared in the same manner as in Example 1, with the exception that chitosan HCl was not used. The amounts of the components are given in Table 5, below (unit: μg). This composition was used as a control for comparison with the composition of the present invention (Example 1).

TABLE 5

|  | C. Ex. 1 |
|---|---|
| Survivin siRNA | 1 |
| Thiamine Pyrophosphate | 2.9 |
| Protamine | 0.6 |
| Lipoid S-100 | 32 |

Comparative Example 2

Preparation of Composition Consisting of Gene, Water-Soluble Chitosan, Protamine, and Phospholipid A composition containing nanoparticles was prepared in the same manner as in Example 1, with the exception that thiamine pyrophosphate was not used. The amounts of the components are given in Table 6, below (unit: μg). This composition was used as a control for comparison with the composition of the present invention (Example 1).

TABLE 6

|  | C. Ex. 2 |
|---|---|
| Survivin siRNA | 1 |
| Chitosan HCl | 17.1 |
| Protamine | 0.6 |
| Lipoid S-100 | 32 |

Comparative Example 3

Preparation of Composition Consisting of Gene, Water-Soluble Chitosan, Thiamine Pyrophosphate, and Phospholipid A composition containing nanoparticles was prepared in the same manner as in Example 1, with the exception that protamine was not used. The amounts of the components are given in Table 7, below (unit: μg). This composition was used as a control for comparison with the composition of the present invention (Example 1).

TABLE 7

|  | C. Ex. 3 |
|---|---|
| Survivin siRNA | 1 |
| Chitosan HCl | 17.1 |
| Thiamine Pyrophosphate | 2.9 |
| Lipoid S-100 | 32 |

Comparative Example 4

Preparation of Composition Consisting of Gene, Water-Soluble Chitosan, Thiamine Pyrophosphate, and Protamine A composition containing nanoparticles was prepared in the same manner as in Example 1, with the exception that phospholipid was not used. The amounts of the components are given in Table 8, below (unit: μg). This composition was used as a control for comparison with the composition of the present invention (Example 1).

TABLE 8

|  | C. Ex. 4 |
|---|---|
| Survivin siRNA | 1 |
| Chitosan HCl | 17.1 |
| Thiamine Pyrophosphate | 2.9 |
| Protamine | 0.6 |

Comparative Example 5

Preparation of Composition Consisting of Gene, Water-Soluble Chitosan, Thiamine Pyrophosphate, Protamine, and Phospholipid The same procedure as in Example 1 was conducted to prepare a composition containing nanoparticles, with the exception that a fluorescein-labeled dsRNA oligomer (FL dsRNA, Invitrogen), instead of survivin siRNA, was used so as to examine inhibitory activity against tumor growth. The amounts of the components are given in Table 9, below (unit: μg). Herein, FL dsRNA had the sequence of 5'-UUG UUU UGG AGC ACG GAA A (dTdT)-3'.

TABLE 9

|  | C. Ex. 5 |
|---|---|
| FL dsRNA | 1 |
| Chitosan HCl | 17.1 |
| Thiamine Pyrophosphate | 2.9 |
| Protamine | 0.6 |
| Lipoid S-100 | 32 |

Comparative Example 6

Preparation of Composition consisting of Gene, Water-Soluble Chitosan, and Thiamine Pyrophosphate The same procedure as in Example 1 was conducted to prepare a composition containing nanoparticles, with the exception that protamine and phospholipid were not used. The amounts of the components are given in Table 10, below (unit: μg). The composition was used as a control for comparison with the composition of the invention (Example 1).

TABLE 10

|  | C. Ex. 6 |
|---|---|
| Survivin siRNA | 1 |
| Chitosan HCl | 17.1 |
| Thiamine Pyrophosphate | 2.9 |

Comparative Example 7

Preparation of Composition Consisting of Gene, Water-Soluble Chitosan, and Phospholipid The same procedure as in Example 1 was conducted to prepare a composition containing nanoparticles, with the exception that thiamine pyrophosphate and protamine were not used. The amounts of the components are given in Table 11, below (unit: μg). The composition was used as a control for comparison with the composition of the invention (Example 1).

TABLE 11

|  | C. Ex. 7 |
|---|---|
| Survivin siRNA | 1 |
| Chitosan HCl | 17.1 |
| Lipoid S-100 | 32 |

EXPERIMENTAL EXAMPLES

Experimental Example 1

Confirmation of Nanoparticles Formation in Composition for Gene Delivery

Nanoparticles formed in the composition prepared in Example 1 were observed by cryo-electron microscopy (Tecnai 12 electron microscope, Philips, Netherlands). The composition of Example 1 was loaded in the form of a thin membrane on a grid and frozen at −170° C. Then, the frozen composition on the grid was observed under an electron microscope according to the instructions of the manufacturer (FIG. 1).

Figure 1:
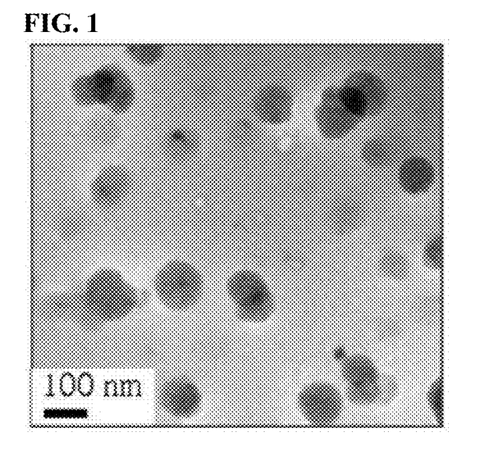
FIG. 1 shows a composition for gene delivery prepared in Example 1 as visualized by cryo-electron microscopy.

As can be seen in FIG. 1, spherical nanoparticles were observed to be formed in the composition for gene delivery comprising a gene, a water-soluble chitosan, a thiamine pyrophosphate, a protamine, and a phospholipid according to the present invention.

Experimental Example 2

Measurement of Nanoparticles Diameter formed in Composition for Gene Delivery

Diameter of nanoparticles formed in the compositions prepared in Examples 1 to 4 and 11 were measured by a particle size analyzer and potentiometer ELS-Z (Electrophoretic Light Scattering Spectrophotometer) (Otsuka, Japan). Particle diameter of the compositions prepared in Examples 1 to 4 and 11 were measured using a particle size cell according to the instructions of the manufacturer (FIG. 2).

Figure 2:
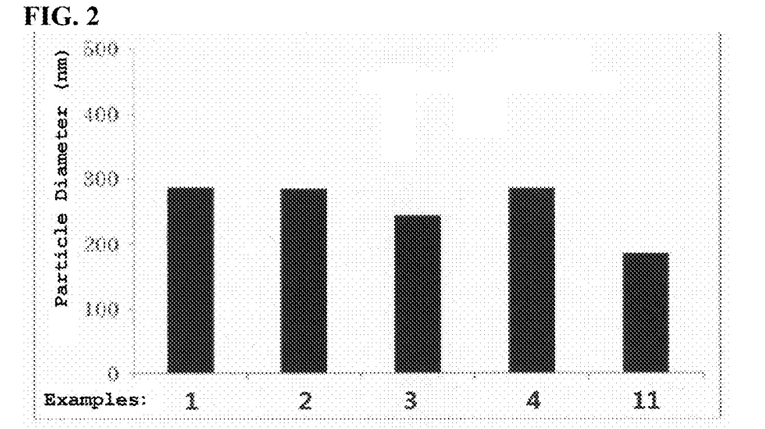
FIG. 2 is graph showing diameters of nanoparticles in compositions for gene delivery prepared in Examples 1, 2, 3, 4, and 11.

As can be seen in FIG. 2, all the compositions for gene delivery comprising a gene, a water-soluble chitosan, a thiamine pyrophosphate, a protamine, and a phospholipid (Examples 1~4) were observed to contain nanoparticles ranging in particle size from 200 to 300 nm with a constant particle distribution. This result indicated that the particles are sufficiently small in size to penetrate into cells and thus are suitable for use in gene delivery.

Experimental Example 3

Measurement of Surface Charge of Nanoparticles in Composition for Gene Delivery

The compositions prepared in Examples 1, 3, and 11 were examined for surface charge by an ELS (Electrophoretic Light Scattering Spectrophotometer) particle size analyzer and potentiometer (ELS-Z, Otsuka, Japan). Surface charges of the composition prepared in Examples 1, 3, and 11 were measured using a zeta potential cell according to the instruction of the manufacturer (FIG. 3).

Figure 3:
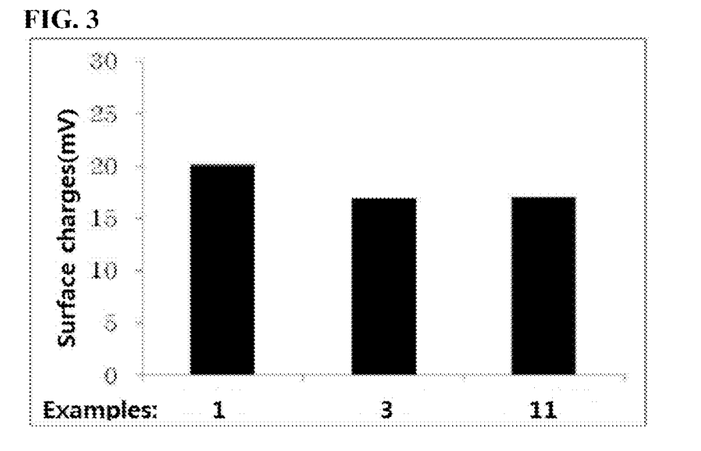
FIG. 3 is a graph showing surface charges on nanoparticles in compositions for gene delivery prepared in Examples 1, 3, and 11.

As can be seen in FIG. 3, nanoparticles in the compositions for gene delivery comprising a gene, a water-soluble chitosan, a thiamine pyrophosphate, and a phospholipid of the present invention were found to have a positive surface charge of 15 mV. This result indicates that the composition of the present invention forms ionic complexes with positive surface charges which allow the ionic complexes to penetrate into cells and thus to deliver a gene to cells.

Experimental Example 4

Confirmation of In Vitro Assay for Inhibitory

Activity of the Composition against Expression of Target Protein

An examination was made of the inhibitory activity of the compositions of Examples 1 and 11, Comparative Examples 1, 2, and 7, and a gene itself against the expression of the target gene using a survivin ELISA kit (R&D systems, catalog No. SVE00) as follows.

A human prostate cancer cell line (PC-3, ATCC) was seeded at a density of 1×105 cells/well into 6-well plates and incubated for 48 hours at 37° C. in a 10% FBS (fetal bovine serum)-supplemented medium under a 5% $CO_2$ atmosphere. The cells were stabilized in a fresh medium (pH 7.2) supplemented with 10% FBS for 2 hours before the application of the genetic agent. Then, the cells were incubated for 48 hours at 37° C. with compositions of Examples 1 and 11, Comparative Examples 1, 2, and 7, and the gene alone, respectively, in a 5% $CO_2$ condition. At this time, the gene therapy drug was used at a dose of 2 μg/well. When the incubation was completed, the medium was removed and the cells in each well were lyzed with 500 μL of a cell lysis buffer (Cell Signaling Technology). After centrifugation of the cell lysates at 12,000 rpm for 20 min, 100 μL of the supernatant separated from cell debris was assayed for the expression level of survivin using a survivin ELISA kit according to the instructions of the manufacturer (FIG. 4).

Figure 4:
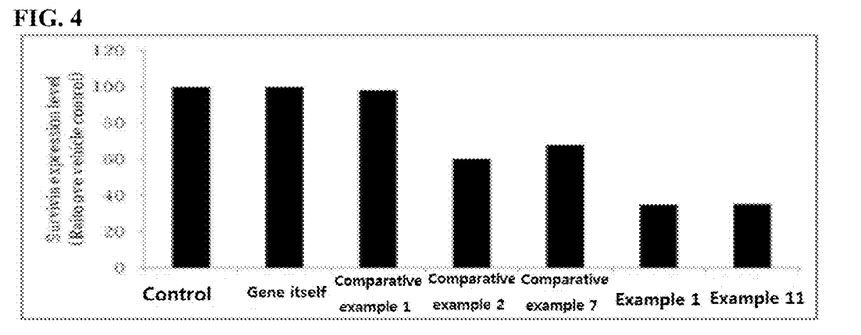
FIG. 4 is a graph showing expression levels of a target protein as compositions delivering a gene, the compositions are prepared in Examples 1 and 11, and Comparative Examples 1, 2, and 7.

As can be seen in FIG. 4, the composition for gene delivery comprising a gene, a water-soluble chitosan, a thiamine pyrophosphate, a protamine, and a phospholipid according to the present invention (Examples 1 and 11) significantly suppressed the expression of the target protein. It indicates that the composition of the present invention can deliver a gene at high efficiency. In contrast, the gene alone and the composition of Comparative Example 1, which was devoid of chitosan, were found to not suppress the expression of the target protein at all. That is, chitosan plays a critical role in the gene delivery, and thus the composition of the present invention cannot perform gene delivery at all without chitosan.

The composition of Comparative Example 2, which was devoid of thiamine pyrophosphate, allowed the target protein to be expressed at a level of 60% as high as that of the control, indicating that the absence of thiamine pyrophosphate weakens the binding affinity between the gene and chitosan at physiological pH (pH 7~7.4), significantly decreasing gene delivery performance. Also, the composition of Comparative Example 7, which was devoid of thiamine pyrophosphate and protamine, expressed the target protein at a level of 68%, and thus was significantly inferior to the composition of the present invention in terms of gene delivery performance.

Experimental Example 5

Assay for Serum Stability of Particles of the Composition for Gene Delivery

Each of the compositions of Examples 1, 3, and 11 and Comparative Examples 2, 3, 4, and 6 was mixed with an equal volume of serum (Invitrogen). After incubation for 3 hours, particle sizes were measured by an ELS (Electrophoretic Light Scattering Spectrophotometer) particle size analyzer and potentiometer (ELS-Z, Otsuka, Japan). In this regard, particle size cells were used according to the instructions of the ELS manufacturer (FIG. 5).

Figure 5:
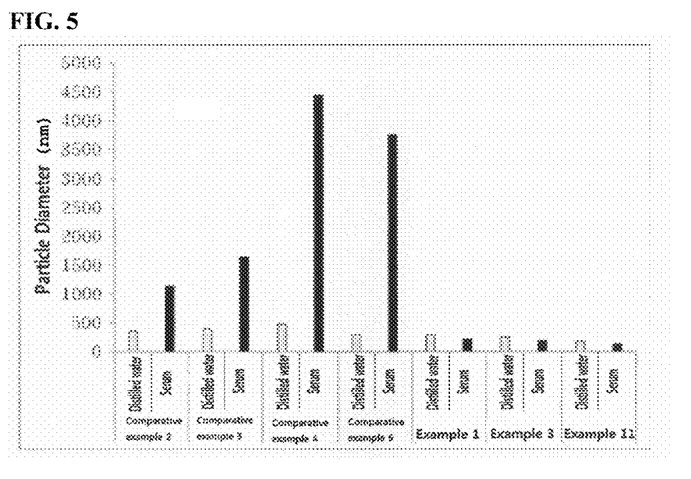
FIG. 5 is a graph showing the stability of the particles prepared in Examples 1, 3, and 11 and Comparative Examples 2, 3, 4, and 6 for gene delivery in serum.

As can be seen in FIG. 5, nanoparticles in the composition of the present invention (Examples 1, 3, and 11) maintained the same original size ranging from 200 to 300 nm even in a serum as in distilled water.

By contrast, as the particles in the composition of Comparative Example 3, devoid of protamine, measured 1,500 nm or more in size, they were observed to significantly aggregate with serum proteins and were not stably maintained. In addition, the particles of Comparative Example 4, devoid of phospholipid, were observed to more seriously aggregate with serum proteins and decrease in stability as their size measured 4,000 nm or greater. Also, serious aggregation with serum proteins and decreased particle stability in the blood were found in the particles of Comparative Example 6, devoid of protamine and phospholipid, which measured 3,000 nm or greater in size. These data suggest that all the components of the composition of the present invention are necessary for preventing aggregation with serum proteins as well as guaranteeing serum stability to the chitosan-based nanoparticle.

A particle size of 1,000 nm or greater showed that the particles of Comparative Example 2, devoid of thiamine pyrophosphate, were also unstable in the blood. In this context, the lack of thiamine pyrophosphate, even though a gene, a water-soluble chitosan, a protamine, and a phospholipid were furnished, caused the complexes to easily dissociate, making them unstable.

Consequently, in order to apply chitosan as a gene carrier for applying in vivo, particle stability is necessary in serum. For this purpose, all the components of the composition of the present invention are necessary.

Experimental Example 6

Lyophilization of the Composition for Gene Delivery and Particle Size Measurement Lyophilized compositions for gene delivery, prepared in Examples 15, 16, and 17, were resuspended in purified water to form a gene concentration of 100 μg/mL, and particle sizes were measured by an ELS (Electrophoretic Light Scattering Spectrophotometer) particle size analyzer and potentiometer (ELS-Z, Otsuka, Japan). In this regard, particle size cells were used according to the instructions of the manufacturer (FIG. 6).

Figure 6:
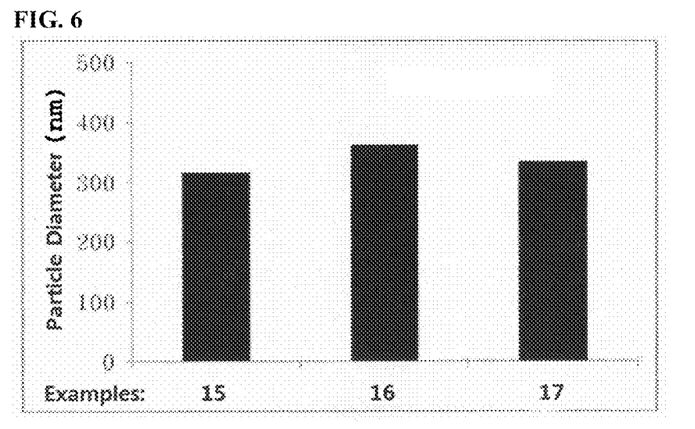
FIG. 6 is a graph showing diameters of the nanoparticles, when the nanoparticles are rehydrated after lyophilization, prepared in Examples 15, 16, and 17 for gene delivery.

As can be seen in FIG. 6, the nanoparticles in the compositions of Examples 15 to 17 maintained a particle size of about 300 nm even though they were rehydrated after lyophilization. That is, the nanoparticles can be stably stored in a lyophilized form in the presence of sugar during distribution and storage. Also, it can be certainly applied in vivo just by resuspending in water.

Experimental Example 7

In Vivo Assay for Inhibitory Activity of the Composition against Tumor Growth

Figure 7:
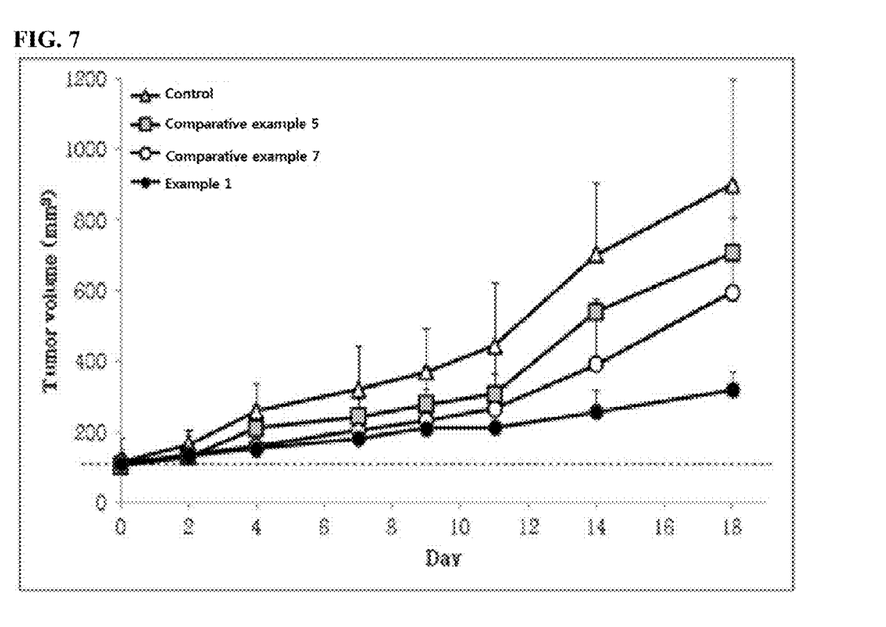
FIG. 7 is a plot showing in vivo gene delivery performance (inhibitory activity against tumor growth) of the composition prepared in Example 1.

For use in evaluating the in vivo gene delivery performance of the compositions of Example 1 and Comparative Examples 5 and 7, prostate cancer cell-implanted immuno-deficient mouse models were constructed. In this context, a prostate cancer cell line was suspended at a density of $2\times10^6$ cells in 50 μL of RPMI and mixed with 50 μL of Matrigel (BD biosciences) before subcutaneous injection into immunedeficient male mice 5 weeks old. Tumors were grown to a volume of 100 mm³, after which the compositions of Examples 1 and Comparative Examples 5 and 7 were injected at a gene dose of 100 μg/mL into the tail vein of three groups of 8 mice. A control group was not administered any composition (non-treated). Each of the gene therapy drugs was injected at a single dose of 40 μg six times over two weeks. Tumor volumes were calculated according to the following formula after long and short axis was measured by calipers (Biomaterials, 2011; 32: 9786-9795).

Tumor volume (mm³)=(short axis²×long axis)/2

The results are shown in FIG. 7. As is understood from the data of FIG. 7, the composition for gene delivery of Example 1 was found to significantly suppress tumor growth in vivo. Notably, the prostate cancer-transplanted immuno-deficient mouse group intravenously injected with the composition of Example 1 was found to have a decrease in tumor volume by about 77% on Day 14 and by about 74% on Day 18, compared to the non-treated group. In contrast, tumor growth was not suppressed but continued to progress in the non-treated group and the group treated with the composition of Example 5, which lacked tumor suppressing activity. The composition of Comparative Example 7, which was devoid of thiamine pyrophosphate and protamine, exhibited a similar effect to that of the composition of Example 1 for one week from the first day of injection, but the tumor growth was suppressed by merely 32% on Day 18, indicating that the composition of Comparative Example 7 is significantly inferior in gene delivery performance to the composition of the present invention.

Also, the results showed that the composition of the present invention could perform excellent gene delivery in vivo even when it was intravenously injected.

Conventional chitosan-based complexes suffer from the disadvantage of having poor binding affinity with genes and being unstable in the blood, and thus cannot be applied to drugs in practice. The present inventors conceived composition for gene delivery that can overcome all of the problems encountered in the prior art. From the present experiment, it proves that composition of the present invention exerts excellent gene delivery performance even when it is systemically administered in vivo.

The invention claimed is:

1. A pharmaceutical composition for gene delivery, comprising:
 (i) a gene;
 (ii) a water-soluble chitosan;
 (iii) a thiamine pyrophosphate or a pharmaceutically acceptable salt thereof;
 (iv) a protamine or a pharmaceutically acceptable salt thereof; and
 (v) a neutral or anionic phospholipid wherein the composition contains nanoparticle complexes ranging in diameter from 10 to 500 nm, and wherein the composition contains the chitosan in an amount of from 10 to 3,000 weight parts, the thiamine pyrophosphate or a pharmaceutically acceptable salt thereof in an amount of from 1 to 1,000 weight parts, the protamine or a pharmaceutically acceptable salt thereof in an amount of from 10 to 1,000 weight parts, and the neutral or anionic phospholipid in an amount of from 100 to 5,000 weight parts, based on 100 weight parts of the gene.

2. The pharmaceutical composition of claim 1, wherein the water-soluble chitosan is selected from the group consisting of chitosan HCl, chitosan acetate, chitosan glutamate or chitosan lactate.

3. The pharmaceutical composition of claim 1, wherein the pharmaceutically acceptable salt of protamine is protamine hydrochloride or protamine sulfate.

4. The pharmaceutical composition of claim 1, wherein the neutral or anionic phospholipid comprises a non-polar tail and a polar head, said non-polar tail having a saturated or unsaturated alkyl ester of 4 to 30 carbon atoms, said polar head having a compound selected from the group consisting of phosphatidylcholine, phosphatidylethanolamine, phosphatidylserine, phosphatidylglycerine, phosphatidylinositol, phosphatidic acid, sphingomyelin, phosphatidylcholine-N-methoxy polyethylene glycol, phosphatidylethanolamine-N-methoxy polyethylene glycol, phosphatidylserine-N-methoxy polyethylene glycol, phosphatidic acid methoxy polyethylene glycol, and a combination thereof.

5. The pharmaceutical composition of claim 1, wherein the gene is selected from the group consisting of a single- or double-stranded DNA, a single- or double-stranded RNA, a plasmid DNA, a single- or double-stranded siRNA, an antisense oligonucleotide, a ribozyme, and a catalytic RNA or nucleotide.

6. The pharmaceutical composition of claim 1, further comprising one or more sugars selected from the group consisting of mannose, glucose, fructose, arabinose, mannitol, sorbitol, sucrose, trehalose, maltose, lactose, cellobiose, isomaltose, dextran, dextrin, α-cyclodextrin, β-cyclodextrin, γ-cyclodextrin, hydroxypropyl-β-cyclodextrin, hydroxyethyl-β-cyclodextrin, dimethyl-β-cyclodextrin, trimethyl-β-cyclodextrin and sulfobutylether β-cyclodextrin.

7. The pharmaceutical composition of claim 1, further comprising one or more additives selected from the group consisting of a stabilizer, a buffer, a preservative, an analgesic and an isotonic agent.

8. The pharmaceutical composition of claim 1, which is in a formulation of an injection, a dripping preparation, an inhalant, or a lyophilized form.

\* \* \* \* \*